(12) United States Patent
Lang et al.

(10) Patent No.: US 8,001,878 B2
(45) Date of Patent: Aug. 23, 2011

(54) KNIFE HOLDER FOR MICROTOME KNIVES AND MICROTOME

(75) Inventors: Anton Lang, Vienna (AT); Reinhard Lihl, Vienna (AT); Paul Wurzinger, Deutsch-Wagram (AT); Andreas Hallady, Vienna (AT)

(73) Assignee: Leica Mikrosystems GmbH, Vienna (AT)

( * ) Notice: Subject to any disclaimer, the term of this patent is extended or adjusted under 35 U.S.C. 154(b) by 1611 days.

(21) Appl. No.: 10/958,073

(22) Filed: Oct. 4, 2004

(65) Prior Publication Data

US 2005/0072285 A1 Apr. 7, 2005

(30) Foreign Application Priority Data

Oct. 7, 2003 (DE) .................................. 103 46 995

(51) Int. Cl.
*B23D 19/00* (2006.01)
(52) U.S. Cl. ........ 83/703; 83/717; 83/698.11; 83/915.5; 83/955
(58) Field of Classification Search .................... 83/451, 83/915.5, 703, 717, 698.11, 699.51, 718, 83/714, 713, 412, 414, 734, 170, 171, 955; 403/303, 304
See application file for complete search history.

(56) References Cited

U.S. PATENT DOCUMENTS

| | | | | |
|---|---|---|---|---|
| 2,517,028 A | * | 8/1950 | Ridner, Sr. | 30/50 |
| 3,902,390 A | * | 9/1975 | Darbo | 83/170 |
| 4,051,755 A | * | 10/1977 | Raveed | 83/167 |
| 4,060,440 A | * | 11/1977 | Behme et al. | 156/154 |
| 4,284,894 A | * | 8/1981 | Sitte et al. | 250/443.1 |
| 4,511,224 A | * | 4/1985 | Sitte et al. | 83/167 |
| 4,532,838 A | * | 8/1985 | Soderkvist | 83/13 |
| 4,738,170 A | * | 4/1988 | Isawa et al. | 82/122 |
| 5,048,300 A | * | 9/1991 | Lihl | 62/48.1 |
| 5,551,326 A | * | 9/1996 | Goodman | 83/167 |
| 6,178,757 B1 | * | 1/2001 | Sitte et al. | 62/126 |
| 7,080,583 B2 | * | 7/2006 | Lihl et al. | 83/13 |
| 7,146,894 B2 | * | 12/2006 | Hendrick et al. | 83/703 |

OTHER PUBLICATIONS

Leica Bruchure—"Reichert Ultracut S/FC S Ultramicrotome and Cryo-Sectioning System", Published Jun. 1991.

* cited by examiner

*Primary Examiner* — Boyer D Ashley
*Assistant Examiner* — Omar Flores-Sánchez
(74) *Attorney, Agent, or Firm* — Hodgson Russ LLP

(57) ABSTRACT

A knife holder (5) for a microtome for cutting samples (4*a*) is disclosed. The knife holder (5) encompasses several knives (2*a*, 2*b*) each of which defines a cutting edge (16). The knife holder (5) is arranged pivotably about a shaft (18); and the shaft (18) is arranged substantially perpendicularly to each cutting edge (16) of the knives (2*a*, 2*b*).

11 Claims, 5 Drawing Sheets

KNIFE HOLDER FOR MICROTOME KNIVES AND MICROTOME

CROSS REFERENCE TO RELATED APPLICATIONS

This application claims priority of the German patent application 103 46 995.8 filed Oct. 7, 2003 which is incorporated by reference herein.

FIELD OF THE INVENTION

The invention concerns a knife holder. The invention concerns in particular a knife holder for microtome knives for cutting samples. Additionally the invention concerns a microtome with the inventive knife holder.

BACKGROUND OF THE INVENTION

Microtomes and ultramicrotomes are, as a rule, equipped with two knives. One knife serves to trim the sample, and the other knife serves to produce the thin sections. Microtomes and/or ultramicrotomes can also be provided with a cooling chamber. During operation of a microtome with a cooling chamber, two or three knives are usually present in the chamber. One is used for trimming, and the second for producing the ultrathin sections. When a new knife is introduced from outside into the cooling chamber, it is necessary to wait a few minutes for temperature stabilization.

In the case of the CR-X chamber of RMC, for a knife change the entire chamber must be displaced laterally by means of a drive. This displacement unit is located at the point on the ultramicrotome at which the chamber is attached. If a base-mounted illumination system is built into the chamber as a presetting aid for the alignment operation between knife and specimen, it is also displaced laterally. The illumination geometry must, however, be maintained exactly while observing the presetting operation with the stereomicroscope. The arrangement of the illumination system can therefore only be a compromise between the two knife positions.

The Leica FCS cooling chamber possesses a capability for displacement of the knife holder in the chamber without modifying the position of the illumination system. In this arrangement, it is possible always to position the knife above the illumination system. This additional displacement capability has, however, the disadvantage that operator errors occur. The knife holder is often displaced along with the illumination system for a knife change, thus disadvantageously modifying the illumination geometry.

During operation of a microtome or ultramicrotome, it is also necessary at regular intervals to replace, after a certain operating time, the knives that are being used. When a cooling chamber is used, operation of the microtome is interrupted during replacement of the knife, since the temperature equilibrium (or "climate") inside the cooling chamber is disturbed by the introduction of the new knife. In addition, it is once again necessary to position, i.e. align, the specimen that is to be cut with respect to the new knife, in accurately positioned and exact fashion. This so-called presetting operation also requires time, and care must be taken that neither the knife nor the specimen is damaged in the process.

SUMMARY OF THE INVENTION

It is therefore the object of the present invention to configure a knife holder in such a way that knives can be changed in simple and precise fashion without a long interruption in the cutting process.

This object is achieved, according to the present invention, by a knife holder for microtome knives for cutting samples, comprising at least two knives are carried by the knife holder, each of which defines a cutting edge, and a shaft being provided by the knife holder about which the knife holder is pivotably arranged, wherein the shaft is arranged substantially perpendicularly to each cutting edge of the at least two knives. It is noted that as used herein, the term "perpendicularly" and alternate forms thereof do not require intersection of two lines or axes, but merely that the lines or axes extend in orthogonal directions relative to one another.

It is a further object of the present invention to configure a microtome which allows an easy and fast changeover of knives without a long interruption in the cutting process.

The above object is achieved by a microtome comprising: a cooling chamber, a knife holder surrounded by the cooling chamber, a sample holder arranged opposite to the knife holder, wherein the knife holder carries at least two knives each of which defines a cutting edge, and a shaft is provided around which the knife holder is pivotably arranged for rotation about an axis extending substantially perpendicularly to each cutting edge.

According to the present invention, a knife holder for a microtome for cutting sample is disclosed, the knife holder carrying several knives each of which defines a cutting edge. The knife holder is arranged pivotably about a shaft, and that shaft is arranged substantially perpendicularly to each cutting edge of the knives. The microtome can also be provided with a cooling chamber. The knife holder is also arranged in the cooling chamber.

It is particularly advantageous that the knife holder carries two knives that are arranged in such a way that their cutting edges are oriented substantially perpendicularly to one another. In addition, the cooling chamber contains respectively a first and a second stop that coact with the knife holder in order thereby to ensure orientation of the knives.

The knife holder encompasses a baseplate in which is embodied a recess by which removal of the knife holder from the cooling chamber is enabled, and can be performed without damage to the sample and/or the sample holder.

BRIEF DESCRIPTION OF THE DRAWINGS

Further advantages and advantageous embodiments of the invention are evident from the dependent claims, and are the subject matter of the Figures below and their descriptions. In the individual Figures:

DETAILED DESCRIPTION OF THE INVENTION

Figure 1:
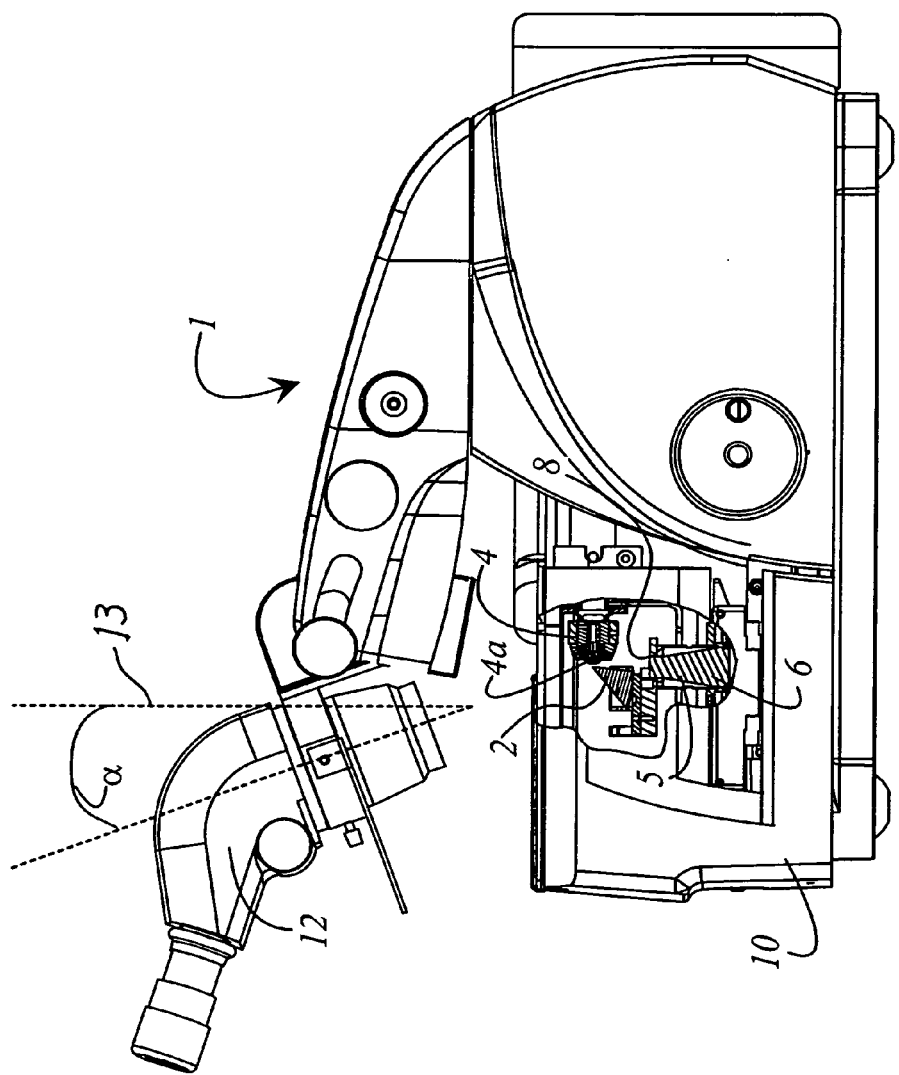
FIG. 1 is a side view of an ultramicrotome with cooling chamber, parts of the cooling chamber being omitted in order to elucidate the association between the knife and sample holder.

FIG. 1 is a side view of a microtome or ultramicrotome 1 having a cooling chamber 10. Parts of cooling chamber 10 are omitted in order to elucidate the association between at least one knife 2 and sample holder 4. The at least one knife 2 is inserted into a knife holder 5. Knife holder 5 is arranged with respect to a base-mounted illumination system 6 in such a way that exit opening 8 of base-mounted illumination system 6 is positioned below knife 2 that is currently in the working position. The working position is defined by the fact that knife 2 is positioned opposite sample holder 4. In the working position, thin sections of a sample 4a that is clamped in sample holder 4 can be produced with the knife.

Microtome 1 is provided with a stereomicroscope 12 that is mounted at a fixed angle a with respect to perpendicular 13. This configuration results in optimum contrast during alignment of knife 2 with respect to the surface of sample 4a that is to be cut. The provision of base-mounted illumination system 6 means that cutting edge 16 of the particular knife 2 that is in the working position can be better detected and, if necessary, oriented with respect to sample 4a.

Figure 2:
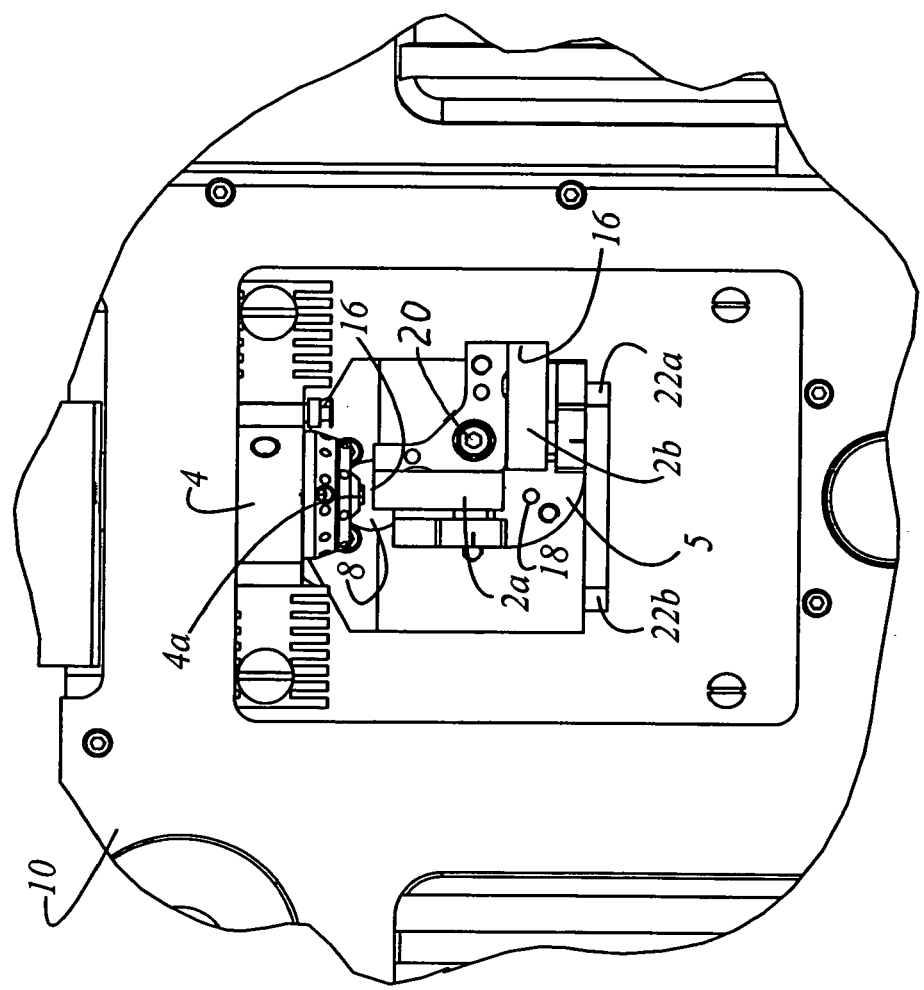
FIG. 2 shows a portion of the cooling chamber from above with the arrangement of the rotatable knife holder in a first position.

FIG. 2 shows a portion of cooling chamber 10 from above, with the arrangement of rotatable knife holder 5 in a first position. Knife holder 5 is pivotable or rotatable about a shaft 18. In the embodiment depicted in FIGS. 2 through 5, knife holder 5 carries a first and a second knife 2a and 2b. Each of knives 2a and 2b has a cutting edge 16. Shaft 18 of knife holder 5 is arranged in such a way that it is substantially perpendicularly to cutting edges 16 of knifes 2a and 2b. Provided between first and second knife 2a and 2b is a screw 20 with which the position of knife holder 5 after pivoting can be additionally immobilized. Provided respectively in cooling chamber 10 are a first and a second stop 22a and 22b with which knife holder 5 coacts, and by means of which a respective knife is positioned with respect to sample 4a clamped in sample holder 4. In the depiction of FIG. 2, sample holder 4 is pivoted in such a way that first knife 2a is positioned opposite sample 4a. Knife holder 5 coacts, in this context, with first stop 22a.

Figure 3:
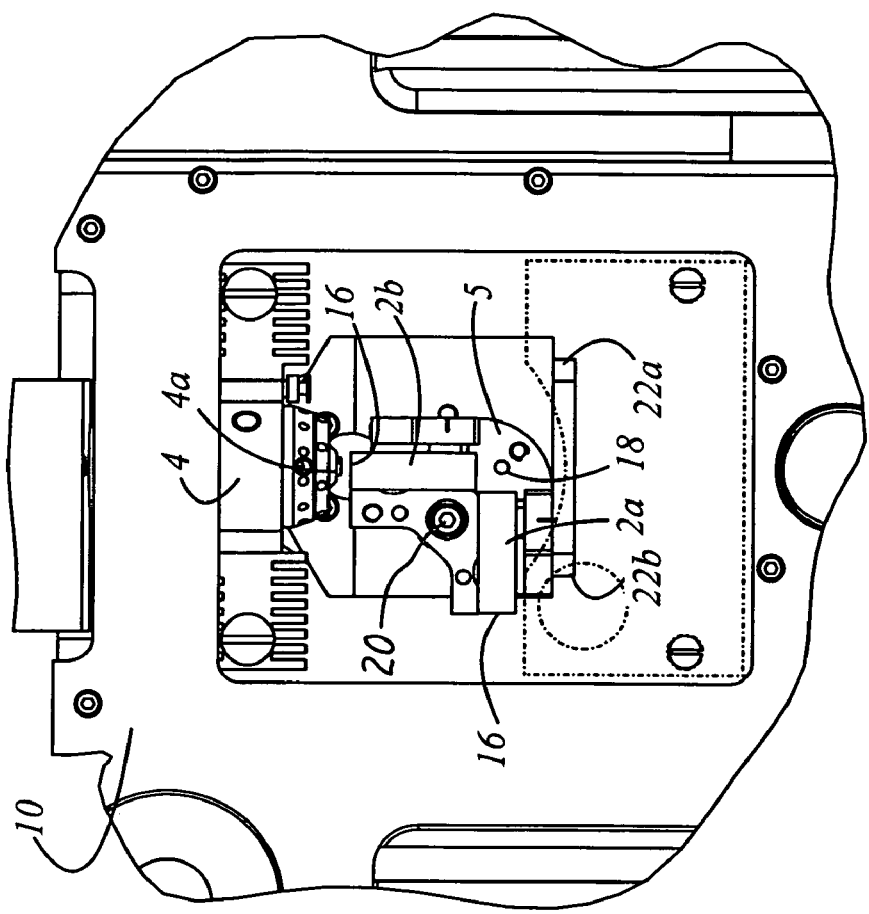
FIG. 3 shows a portion of the cooling chamber from above with the arrangement of the rotatable knife holder, the knife holder being pivoted 90 degrees with respect to the first position of FIG. 2.

FIG. 3 shows a portion of cooling chamber 10 from above, with the arrangement of rotatable knife holder 5, knife holder 5 being rotated 90 degrees with respect to the first position in FIG. 2. Second knife 2b is here positioned opposite sample 4a.

Figure 4:
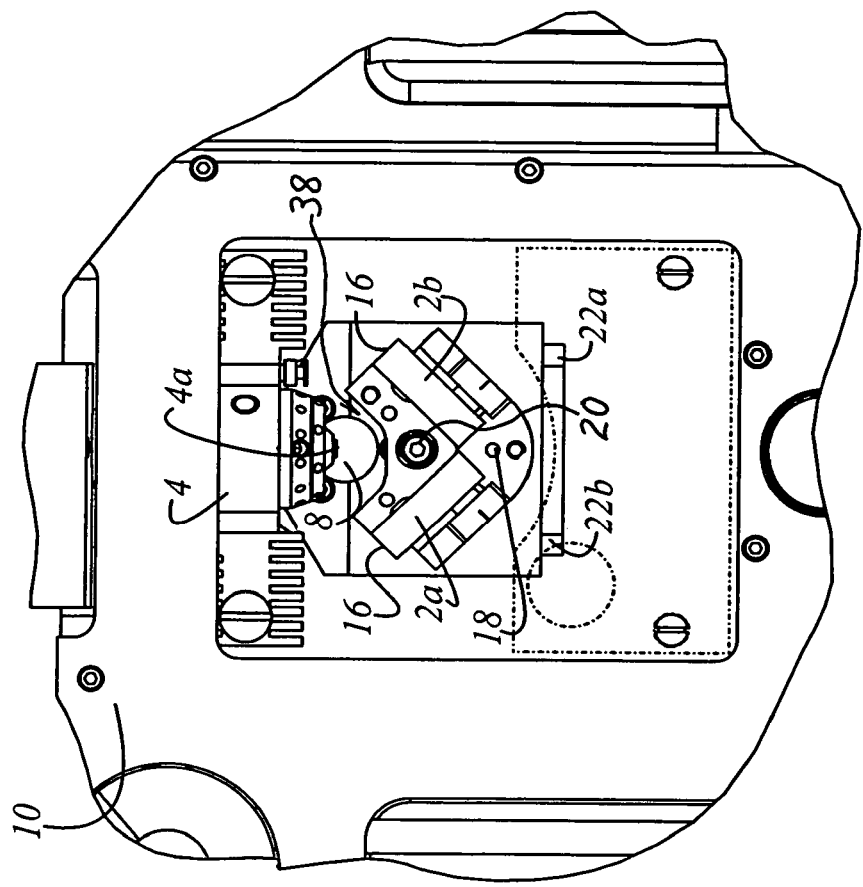
FIG. 4 shows a portion of the cooling chamber from above with the arrangement of the rotatable knife holder, the knife holder being pivoted into a removal position.

FIG. 4 shows a portion of cooling chamber 10 from above. Rotatable knife-holder 5 is pivoted into a removal position. Knife holder 5 is pivoted 45 degrees so that first and second knife 2a and 2b are positioned respectively on either side of sample 4a. Knife holder 5 can thus easily be lifted upward out of cooling chamber 10.

Figure 5:
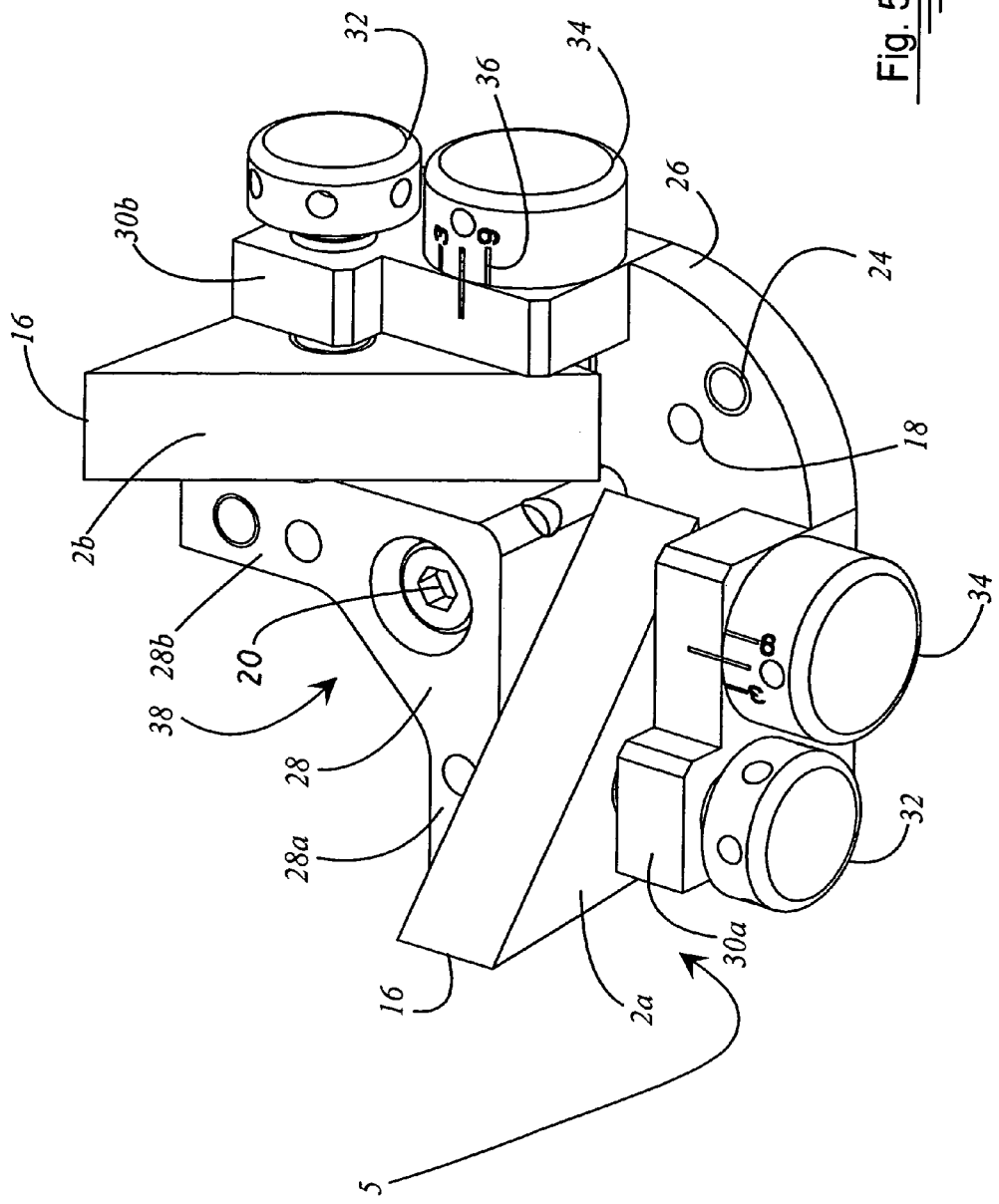
FIG. 5 is a three-dimensional view of the knife holder according to the present invention.

FIG. 5 is a three-dimensional view of knife holder 5 according to the present invention. The two knives 2a and 2b are arranged at an angle of 90 degrees to one another. Knife holder 5 is rotatable about shaft 18. With screw 20, knife holder 5 can be immobilized in a selected position in cooling chamber 10. Knife holder 5 is furthermore provided with a thread 24 into which a removal aid (not depicted) for knife holder 5 can be threaded. Knife holder 5 comprises a baseplate 26 on which an angle element 28 is embodied. Angle element 28 possesses a first and second limb 28a and 28b. First knife 2a rests against first limb 28a, and second knife 2b against second limb 28b. A first block 30a is spaced away from first limb 28a. A second block 30b is spaced away from second limb 28b. First and second block 30a and 30b are each engaged by a clamping knob 32 adjustably connected to respective limbs 28a and 28b, whereby first knife 2a and second knife 2b are respectively pressable against first and second limbs 28a and 28b. Clamping of first and second knife 2a and 2b is achieved with knob 32. Provided on each block 30a and 30b, in addition to clamping knob 32, is an angle adjustment knob 34 operatively connected to the associated microtome knife 2a or 2b, and on which a scale 36 is provided. The relief angle of the two knives 2a and 2b is respectively adjustable with associated angle adjustment knob 34. Baseplate 26 moreover possesses a recess 38. As depicted in FIG. 4, knife holder 5 is pivoted into a position such that the entire knife holder 5 can be removed from cooling chamber 10. In this case recess 38 of baseplate 26 is oriented so that exit opening 8 of base-mounted illumination system 6 is completely visible.

What is claimed is:

1. An apparatus for carrying at least two microtome knives each having a cutting edge, the apparatus comprising:
   a knife holder including means for fixing the at least two microtome knives to the knife holder such that the respective cutting edges of the two microtome knives are oriented substantially perpendicularly to one another;
   a shaft;
   wherein the knife holder is pivotally mounted on the shaft for rotation about an axis extending substantially perpendicularly to each cutting edge of the at least two microtome knives and;
   wherein the knife holder includes a baseplate and an angle element mounted on the baseplate, the angle element having a first limb and a second limb, and wherein the knife holder further includes a first block opposite the first limb and a second block opposite the second limb.

2. An apparatus for carrying at least two microtome knives each having a cutting edge, the apparatus comprising:
   a knife holder including means for fixing the at least two microtome knives to the knife holder such that the respective cutting edges of the two microtome knives are oriented substantially perpendicularly to one another;
   a shaft;
   wherein the knife holder is pivotally mounted on the shaft for rotation about an axis extending substantially perpendicularly to each cutting edge of the at least two microtome knives and;
   wherein the knife holder includes a baseplate and an angle element mounted on the baseplate, the angle element having a first limb and a second limb, and wherein the knife holder further includes a first block opposite the first limb and a second block opposite the second limb; and
   a first clamping knob adjustably connected to the first limb and arranged to engage the first block for clamping a first microtome knife between the first limb and the first block, and a second clamping knob adjustably connected to the second limb and arranged to engage the second block for clamping a second microtome knife between the second limb and the second block.

3. An apparatus for carrying at least two microtome knives each having a cutting edge, the apparatus comprising:
   a knife holder including means for fixing the at least two microtome knives to the knife holder such that the respective cutting edges of the two microtome knives are oriented substantially perpendicularly to one another;
   a shaft;
   wherein the knife holder is pivotally mounted on the shaft for rotation about an axis extending substantially perpendicularly to each cutting edge of the at least two microtome knives and;
   wherein the knife holder includes a baseplate and an angle element mounted on the baseplate, the angle element having a first limb and a second limb, and wherein the knife holder further includes a first block opposite the first limb and a second block opposite the second limb; and a first angle adjustment knob mounted on the first block and operatively connected to a first microtome knife for adjusting a relief angle of the first microtome knife, and a second angle adjustment knob mounted on the second block and operatively connected to a second microtome knife for adjusting a relief angle of the second microtome knife.

4. A microtome comprising:

a cooling chamber;

a knife holder surrounded by the cooling chamber;

at least two microtome knives carried by the knife holder, each of the at least two microtome knives being identical to each other and having a cutting edge, the respective cutting edges of the two microtome knives extending substantially perpendicularly to one another;

a sample holder arranged opposite to the knife holder; and a shaft on which the knife holder is pivotably arranged for rotation about an axis extending substantially perpendicularly to each of the cutting edges;

wherein the cooling chamber includes a first stop arranged to engage the knife holder to position a first microtome knife opposite the sample holder and a second stop arranged to engage the knife holder to position a second microtome knife opposite the sample holder.

5. The microtome as defined in claim 4, wherein the knife holder includes a baseplate having a recess by which removal of the knife holder from the cooling chamber is facilitated.

6. The microtome as defined in claim 4, wherein the knife holder is rotatable between two angular positions 90 degrees apart so that one of the at least two microtome knives is respectively located opposite the sample holder in each of the two angular positions.

7. The microtome as defined in claim 4, further comprising a stereomicroscope arranged for observing a sample in the sample holder and the cutting edge of a microtome knife positioned opposite the sample holder.

8. The microtome as defined in claim 4, wherein the microtome is an ultramicrotome.

9. A microtome comprising:

a cooling chamber;

a knife holder surrounded by the cooling chamber, wherein the knife holder includes a baseplate having a recess by which removal of the knife holder from the cooling chamber is facilitated;

at least two microtome knives carried by the knife holder, each of the at least two microtome knives being identical to each other and having a cutting edge, the respective cutting edges of the two microtome knives extending substantially perpendicularly to one another;

a sample holder arranged opposite to the knife holder; and a shaft on which the knife holder is pivotably arranged for rotation about an axis extending substantially perpendicularly to each of the cutting edges;

wherein the knife holder includes an angle element mounted on the baseplate, the angle element having a first limb and a second limb, and wherein the knife holder further includes a first block opposite the first limb and a second block opposite the second limb.

10. The microtome as defined in claim 9, further comprising a first clamping knob adjustably connected to the first limb and arranged to engage the first block for clamping a first microtome knife between the first limb and the first block, and a second clamping knob adjustably connected to the second limb and arranged to engage the second block for clamping a second microtome knife between the second limb and the second block.

11. The microtome defined in claim 9, further comprising a first angle adjustment knob mounted on the first block and operatively connected to a first microtome knife for adjusting a relief angle of the first microtome knife, and a second angle adjustment knob mounted on the second block and operatively connected to a second microtome knife for adjusting a relief angle of the second microtome knife.

* * * * *